United States Patent [19]

Hartness

[11] 4,285,230
[45] Aug. 25, 1981

[54] BOTTLE TESTER

[75] Inventor: Thomas S. Hartness, Greenville, S.C.

[73] Assignee: Hartness International, Inc., Greenville, S.C.

[21] Appl. No.: 71,942

[22] Filed: Sep. 4, 1979

[51] Int. Cl.³ .............................................. G01M 3/26
[52] U.S. Cl. ........................................ 73/49.4; 73/37; 73/49.2
[58] Field of Search ................. 73/49.2, 49.4, 49.3, 73/45.4, 45, 37

[56] References Cited

U.S. PATENT DOCUMENTS

| | | | |
|---|---|---|---|
| 2,048,027 | 7/1936 | Preston | 73/49.4 |
| 2,084,653 | 6/1937 | Preston | 73/49.4 |
| 2,314,310 | 3/1943 | Jackson et al. | 73/37 |
| 3,060,735 | 10/1962 | Baker | 73/149 |
| 3,683,677 | 8/1972 | Harris | 73/49.2 |
| 3,751,973 | 8/1973 | Strauss et al. | 73/45 |
| 3,762,213 | 10/1973 | Nowicki | 73/45.3 |
| 3,771,649 | 11/1973 | Strauss | 73/37 X |
| 3,805,593 | 4/1974 | Sandoz et al. | 73/49.2 |
| 3,805,594 | 4/1974 | Hayashi | 73/49.2 |
| 3,894,424 | 7/1975 | Taylor et al. | 73/49.2 |
| 3,895,514 | 7/1975 | Northup | 73/49.4 |
| 3,943,819 | 3/1976 | Charron | 85/62 |
| 3,951,185 | 4/1976 | Bower et al. | 73/49.2 X |
| 3,954,004 | 5/1976 | Orner | 73/141 A X |
| 4,090,394 | 5/1978 | Herman et al. | 73/37 |

Primary Examiner—Gerald Goldberg
Assistant Examiner—Joseph W. Roskos
Attorney, Agent, or Firm—Bailey, Dority & Flint

[57] ABSTRACT

A tester for testing the physical characteristics of bottles such as the degree of stretch of a plastic bottle and the pressure required for rupturing a glass bottle. The apparatus includes an elongated cylinder having a bore extending therethrough. A piston is threadably carried within the bore so that when the lower end of the cylinder is secured to the top portion of a bottle, the piston is in axial alignment with the bottle. Upon feeding the piston into the bottle filled with an incompressible fluid, pressure is exerted on the interior of the bottle stretching or exploding the bottle depending on the test being performed.

5 Claims, 8 Drawing Figures

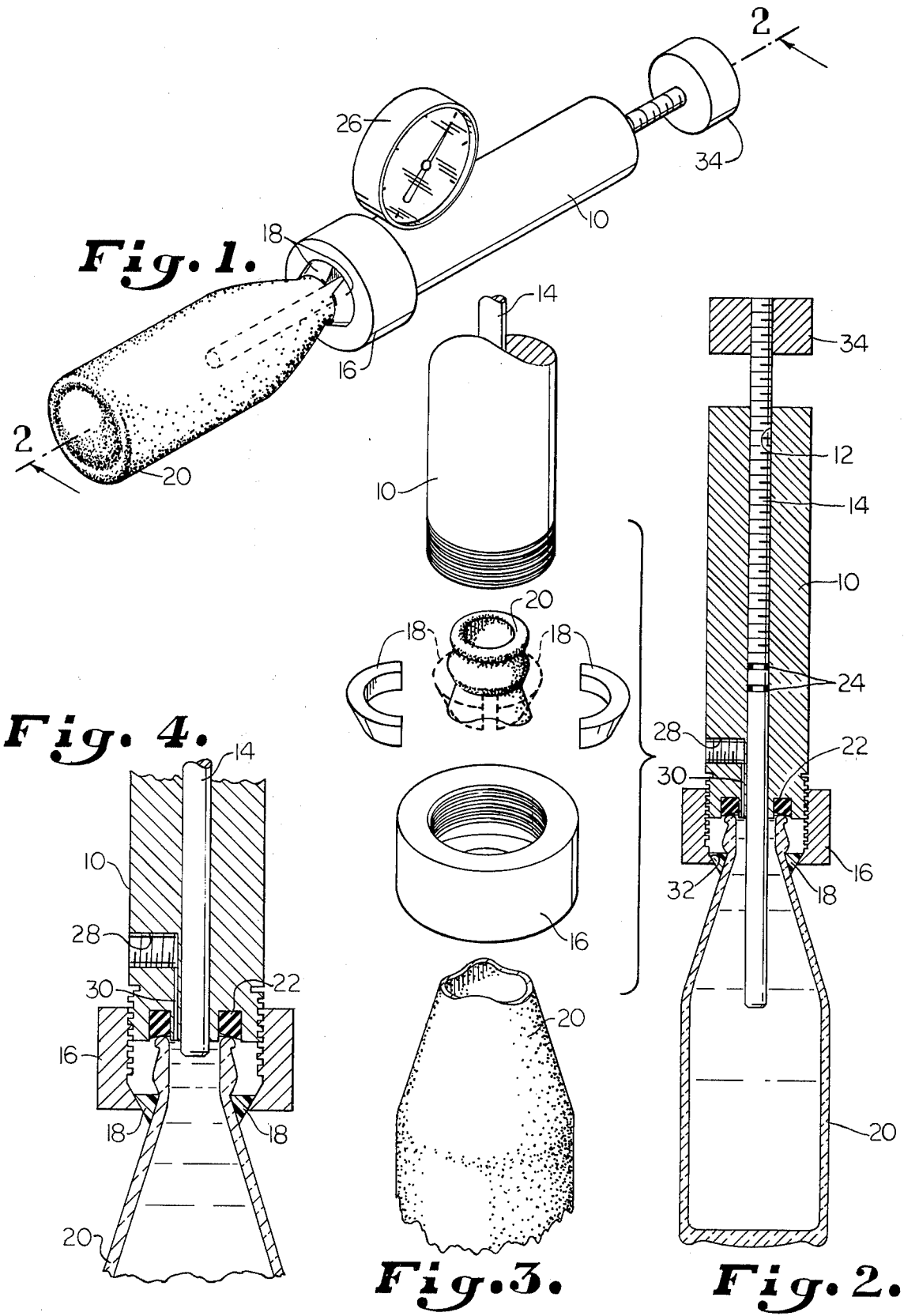

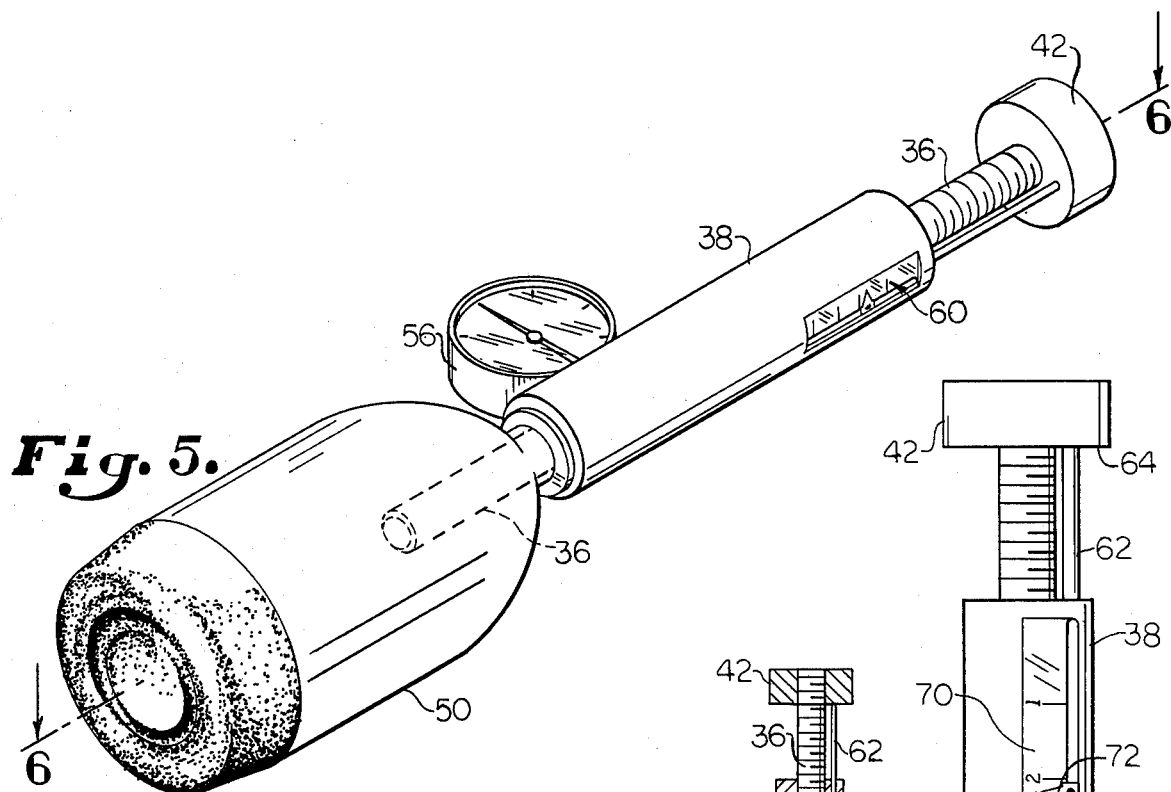
Fig. 5.
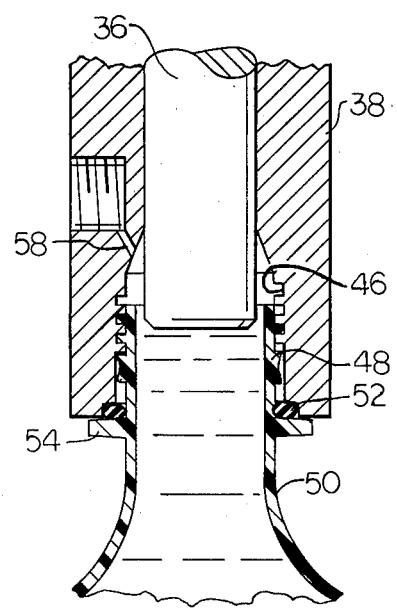
Fig. 7.
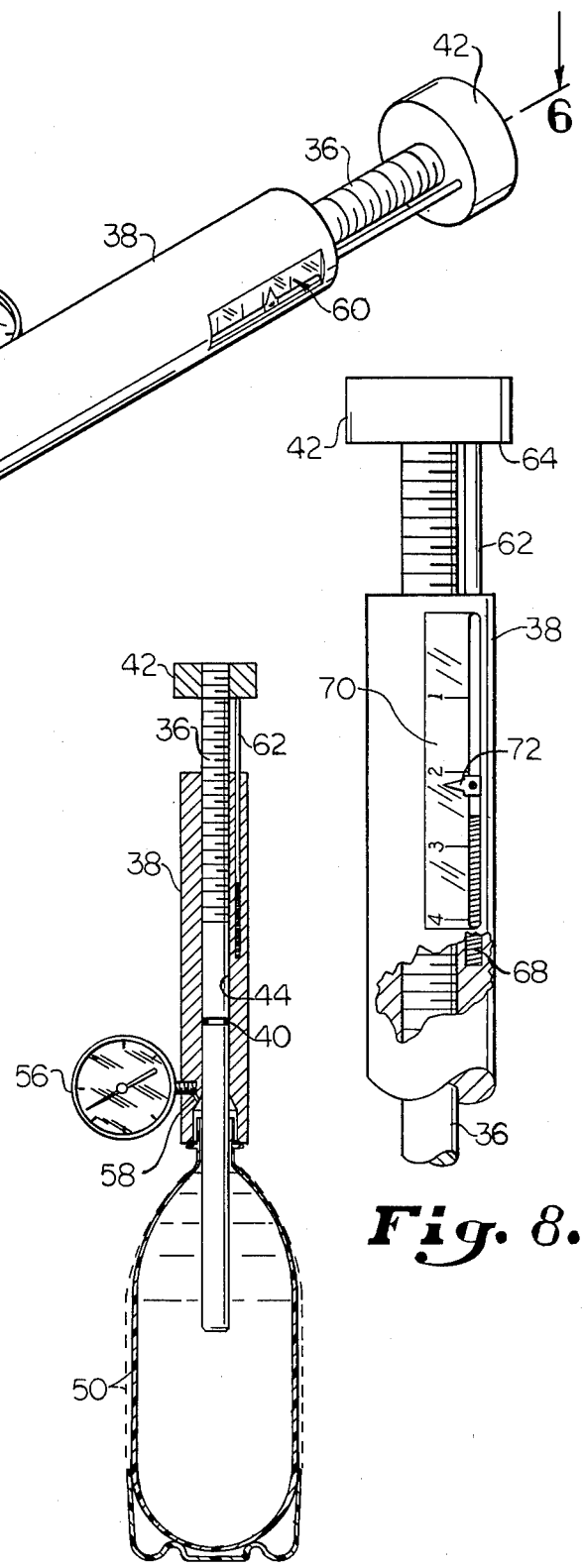
Fig. 8.
Fig. 6.

BOTTLE TESTER

BACKGROUND OF THE INVENTION

Many attempts have been made in the past for testing the characteristics of a bottle such as the degree of stretch on plastic bottles that takes place when they are pressurized. One such device is disclosed in U.S. Pat. No. 4,090,394 wherein pressurized fluid is forced into a plastic bottle by means of a piston and by sensing the movement of the piston the amount of stretch in the bottle can be determined.

In U.S. Pat. No. 3,894,424, hydrostatic pressure is utilized for testing the strength of bottles and the like. One problem with both of these devices is that they are relatively fixed structures.

Other volumetric testing devices for bottles and leak detectors are disclosed in U.S. Pat. Nos. 3,060,735, 3,683,677, 3,751,973, 3,951,185, 3,762,213, 3,805,593, 3,943,819 and 3,954,004.

SUMMARY OF THE INVENTION

Apparatus for manually testing the physical characteristics of bottles and, in particular, the degree that plastic bottles stretch under pressure and the pressure required for testing glass bottles to the rupture point. In one embodiment which is used for testing the pressure required for rupturing a bottle, it includes an elongated cylinder which has a bore extending axially therethrough. A piston is threadably carried in the elongated bore and extends out an upper end of the cylinder. Positioned on the upper end of the piston is a knob that is used for rotating the piston for feeding the piston out of the lower end of the cylinder into the bottle.

Means is carried on the lower end of the cylinder for attaching the cylinder to the bottom. In one particular embodiment, this means includes a collar which is threadably carried on the lower end of the cylinder. A pair of plastic chucks are carried within the collar and have tapering inner edges which mesh flush against the neck of a bottle being tested for securely holding the bottle on the bottom of the cylinder.

A seal is carried on the bottom of the cylinder for providing a seal between the cylinder and the top of the bottom.

A pressure gauge is carried by the cylinder and communicates with the interior of the bottle through a passage. During the test, incompressible fluid such as water is filled to the top of the bottle. As the piston is rotated, it is fed into the bottle causing the pressure within the bottle to increase until an acceptable pressure as set by the industry is reached or the bottle ruptures. The rupture point of the bottle is recorded on the pressure gauge.

A second embodiment of the invention is utilized for testing or registering the degree that a plastic bottle stretches upon being pressurized such as normally would occur when the bottle is being filled with a carbonated drink. In this particular embodiment, the lower end of the cylinder is threaded for receiving the threaded top of the bottle. A pressure gauge communicates with the interior of the bottle by means of a passage extending through the lower portion of the cylinder. Prior to commencing the tests, the bottle is filled with an incompressible fluid such as water and the water brims over the top. The knob carried on the top of a piston is rotated feeding the piston down into the bottle. The knob continues to be rotated until pressure on the pressure gauge reaches the pressure of approximately 55 lbs./sq. in. which is the normal pressure encountered during filling the bottle. Upon reaching this pressure, a reading is taken off of a separate gauge which measures the longitudinal movement of the piston into the bottle. This gauge is precalculated so that the readings thereon correspond to the volumetric displacement made by the piston entering into the bottle. This, of course, corresponds to the stretch of the walls of the bottle.

Accordingly, it is an important object of the present invention to provide a portable device for readily testing the physical characteristics of bottles.

Another important object of the present invention is to provide a relatively simple and small device for testing bottles for determining whether or not a bottle will withstand specified pressure.

Another important object of the present invention is to provide a bottle stretch tester which determines the degree of stretch of plastic bottle upon being pressurized.

Still another important object of the present invention is to provide a very simple, accurate and inexpensive tester for testing the physical characteristics of bottles.

These and other objects and advantages of the invention will become apparent upon reference to the following specification, attendant claims and drawings.

BRIEF DESCRIPTION OF THE DRAWINGS

FIG. 1 is a perspective view of a glass bottle pressure tester contructed in accordance with the present invention.

FIG. 2 is a sectional view taken along line 2—2 of FIG. 1

FIG. 3 is an exploded view illustrating the manner in which a bottle is secured to the pressure testing device of FIG. 1.

FIG. 4 is an enlarged sectional view illustrating the position of a piston forming part of the tester at the beginning of the test.

FIG. 5 is a perspective view of a modified form of the invention illustrating a plastic bottle stretch tester.

FIG. 6 is a sectional view taken along lines 6—6 of FIG. 1.

FIG. 7 is an enlarged sectional view illustrating the position that the piston takes at the time of commencing the test.

FIG. 8 is an enlarged elevational view illustrating the gauge for registering the degree of penetration of the piston into the bottle during the stretch test.

DESCRIPTION OF A PREFERRED EMBODIMENT

Referring to FIG. 1 of the drawing, there is illustrated a glass bottle pressure tester which includes a cylindrical cylinder 10 that has an elongated bore 12 extending therethrough. The upper end of the bore 12 is threaded for receiving a piston 14. The piston 14 has threads on a portion thereof which threadably engage the threads carried on the inner wall of the bore 12.

A collar 16 is threadably carried on the lower end of the cylinder and has a pair of semi-circular chucks 18 carried therein which engage the upper neck portion of a bottle 20 for securing the bottle to the bottom of the cylinder. A circular seal 22 is recessed in the base of the cylinder for providing a seal between the top of the bottle and the bottom of the cylinder 10. O-rings 24 are carried on the piston for providing a seal between the lower portion of the piston 14 and the inner wall of the bore 12.

A pressure gauge 26 is secured to the cylinder by means of a threaded nipple which threads within a threaded lateral extending bore 28. A passage 30 extends from the bore 28 into the top of the bottle for providing communication between the pressure gauge 26 and the interior of the bottle.

It is noted that the chucks 18 are tapered adjacent their inner surfaces to fit flush against the wall of the bottle being tested and have an outer surface which is tapered to fit within a complementary tapered portion 32 carried adjacent the bottom of the retaining collar 16. The chucks 18 are made of plastic so as not to scratch or damage the neck of the bottle.

In order to test the bottle, the bottle is placed with the top adjacent the seal 22. The chucks 18 are pressed against the wall of the bottle and the collar 16 is screwed onto the bottom of the cylinder pulling the top of the bottle tightly against the seal 22 and firmly securing the bottle on the end of the cylinder. It is to be understood that as a result of using the chucks 18, various shapes and sizes of bottles can be tested. Prior to the bottle being placed on the end of the cylinder, it is filled completely with an incompressible fluid such as water with the water brimming over the top. At the commencement of the tests, the piston extends approximately $\frac{1}{4}''$ out of the end of the cylinder. The purpose of the piston extending slightly into the bottle is to ensure that there is no air left in the bottle, and it is completely filled with water. The reason for this is that if an air gap is left in the bottle, the bottle tends to explode rather than rupture. It is intended that the bottle be tested with hydrostatic pressure.

The bottle is then lowered into a protective housing which may be a larger plastic bottle covered with a cloth bag. The piston is then rotated by rotating a knob 34 carried on top thereof. As the knob is rotated clockwise, the piston is fed into the bottle causing the pressure exerted through the liquid to gradually build up. For each particular bottle, there is a standard pressure that it should withstand prior to rupturing and during the test, the pressure is increased by rotating the knob 34 until it reaches slightly below that particular pressure setting for that particular bottle. The knob 34 is then rotated slower until the bottle reaches an acceptable pressure or ruptures. Since the bottle is pressurized hydrostatically, instead of exploding, it merely breaks with very little explosive force and is retained within the protective plastic housing or bag. The bottle can be observed after the test to determine its weakest point. In one particular test, the bottle ruptured at approximately 400 p.s.i. and it ruptured adjacent the bottom thereof indicating that this was the weakest point of the bottle.

One advantage of the particular bottle tester illustrated is that the bottle is firmly secured to the cylinder by the collar 16 and the operator merely has to rotate the knob 34 in performing the test.

Another advantage of this particular pressure tester is that the speed that the pressure is increased when you are approaching the pressure where you anticipate the bottle to rupture can be slowed to a very slow rate whereas when pumps are utilized, complicated controls are required.

Referring to FIG. 5 of the drawing, there is illustrated a modified form of the invention wherein the device is utilized for stretch testing plastic bottles. In this particular device, a threadable piston 36 extends into an elongated cylinder 38 which has threads on its upper end for receiving the piston. The lower end of the piston is smooth and is sealed to the interior of the bore by means of an O-ring 40. A knob 42 is provided on the top of the piston for rotating the piston. The lower end of the bore 44 extending through the cylinder 38 is enlarged as illustrated by the threads 46 so that the threaded top 48 of a bottle 50 can be screwed therein. An O-ring 52 is provided adjacent the bottom of the cylinder for providing a seal between a radially extending flange 54 provided on the bottle and the bore extending through the cylinder. A pressure gauge 56 is screwed into the side of the cylinder and communicates with the interior of the bottle through a small passage 58.

In order to measure the volumetric displacement or expansion of the bottle 50, the depth of extension or penetration of the piston 36 into the bottle is registered. This is registered on a depth gauge generally designated by the reference character 60 that is carried on the side of the cylinder 38. The depth gauge includes a spring loaded rod 62 which extends out of a bore for being engaged by a lower surface 64 of the knob 42 as the knob is rotated. The knob forces the rod 62 downwardly against a spring 68 as it is rotated. A calibrated scale 70 is provided on the side of the cylinder and a pointer 72 which is directly connected to the rod 62 indicates the depth of penetration of the piston 36 into the bottle 50. The expansion of the bottle is directly proportional to the depth of penetration of the piston 36 into the bottle since prior to commencing the test, the bottle is filled to its brim with an incompressible fluid such as water.

It is important that a bottle not stretch beyond predetermined tolerances at predetermined pressures so as to control exactly the amount of liquid deposited therein when being filled.

Normally, when filling plastic bottles with carbonated drinks, the plastic bottle is pressurized to approximately 55 p.s.i., therefore, it is desirable to routinely test the bottles being run on the bottle filling machine to determine the degree of stretch at this particular pressure. In order to test the bottle with the device shown in FIG. 5 through 8, the plastic bottle is first filled to its top with water and screwed into the bottom of the cylinder 38. The knob 42 is rotated causing the piston to be extended into the bottle. As the piston is extended into the bottle 50, the pressure registering on the gauge 56 increases. When the pressure reaches a reading of approximately 55 p.s.i., depending on the particular bottle being tested, the depth that the piston extends into the bottle is read on the guage 60. If the reading is within certain predetermined tolerances, then the bottle is approved.

While the drawings and description pertain primarily to glass and plastic bottles, it is to be understood that the device could be used for testing metal bottles or cylinders provided for $CO_2$ and pressurized air.

While a preferred embodiment of the invention has been described using specific terms, such description is for illustrative purposes only, and it is to be understood that changes and variations may be made without departing from the spirit or scope of the following claims.

What is claimed is:

1. A hand-held apparatus for manually testing the physical characteristics of the wall of a bottle by pressurizing fluid carried therein, said bottle having a main body with a neck integral therewith which terminates in an opened top, said apparatus comprising:

an elongated cylinder;

a bore extending axially through said elongated cylinder;

threads carried on a portion of said cylinder surrounding said bore;

a piston carried in said elongated bore and extending out an upper end of said cylinder;

threads carried on a portion of said piston meshing with said threads carried on a portion of said cylinder surrounding said bore;

means for attaching a lower end of said cylinder to the top of said bottle with said piston being axially aligned with the top of said bottle;

seal means sealing said cylinder to the top portion of said bottle; and hand operated means for rotating said piston feeding a lower end of said piston into said bottle gradually pressurizing said fluid as said piston is inserted into said bottle;

whereby the effect of pressure on the wall of said bottle can be monitored.

2. The apparatus as set forth in claim 1 further comprising:

a pressure gauge carried by said cylinder, and a passage carried in a lower portion of said cylinder providing communication between the interior of said bottle and said pressure gauge, whereby said pressure gauge registers the pressure that is imparted to the wall of said bottle as said piston is fed therein.

3. The apparatus as set forth in claim 1 further comprising:

a gauge connected to said piston registering the longitudinal extension of said piston into said bottle;

whereby the volumetric displacement of said bottle can be registered responsive to changes in pressure.

4. The apparatus as set forth in claim 1 wherein said means for attaching a lower end of said cylinder to said bottle comprises:

a collar threadably carried on a lower end of said cylinder;

a pair of semicircular chucks carried in said collar engaging said neck of said bottle for supporting said bottle and aligning said top of said bottle with said piston.

5. The apparatus as set forth in claim 4 wherein said means for rotating said piston comprises:

an enlarged knob carried on an upper end of said piston which, upon rotating, feeds said piston into said bottle increasing the pressure imparted through said fluid until an acceptable pressure is reached or said bottle ruptures.

* * * * *